United States Patent [19]

Orlowski et al.

[11] 4,125,626

[45] Nov. 14, 1978

[54] SYNTHESIS AND USE OF L-γ-GLUTAMYL-DOPA

[75] Inventors: Marian Orlowski; Sherwin Wilk, both of New York, N.Y.

[73] Assignee: Mt. Sinai School of Medicine of the City University of New York, New York, N.Y.

[21] Appl. No.: 759,831

[22] Filed: Jan. 17, 1977

[51] Int. Cl.² .......................................... A61K 31/195
[52] U.S. Cl. .................................................. 424/319
[58] Field of Search ........................................ 424/319

[56] References Cited

U.S. PATENT DOCUMENTS

| | | | |
|---|---|---|---|
| 3,676,492 | 7/1972 | Biel et al. | 424/324 |
| 3,769,424 | 10/1973 | Bayne | 424/319 |
| 3,803,120 | 4/1974 | Felix | 424/324 |
| 3,939,253 | 2/1976 | Bodor | 424/319 |
| 3,947,590 | 3/1976 | Kynel et al. | 424/319 |

OTHER PUBLICATIONS

Christenson et al., Archives of Biochemistry & Biophysics, vol. 141, pp. 356–367 (1970).
Orlowski et al., Acta Biochemica Polonica, vol. VIII, No. 2 (1961), pp. 189–200.
Orlowski, Archivum Immanolograe et Therapiae Experimentalis, 1963, vol. 11, pp. 1–61.
International Encyclopedia of Pharmacology & Therapeutics, vol. 1, published by Pergamon Press, N.Y. (1974), pp. 82–84.

*Primary Examiner*—Donald B. Moyer
*Attorney, Agent, or Firm*—Brumbaugh, Graves, Donohue and Raymond

[57] ABSTRACT

The synthesis of L-γ-glutamyl-DOPA (L-γ-glutamyl-L-3,4-dihydroxy-phenylalanine) and its use selectively to increase renal blood flow in mammals.

2 Claims, No Drawings

SYNTHESIS AND USE OF L-γ-GLUTAMYL-DOPA

BACKGROUND OF THE INVENTION

At the present time, there are drugs available which affect the metabolism of kidney cells, influence renal blood flow, alter water and electrolyte excretion and other functions of the kidney. A serious drawback of some of these drugs is that they exert their pharmacological activity on parts of the system other than the kidney and thereby cause toxicities and undesirable systemic side effects such as acceleration in heart rate, and elevation of blood pressure.

Such problematic systemic effects are often reported in the pharmacology of dopamine (Formula I) and its metabolic precursor L-DOPA (Formula II).

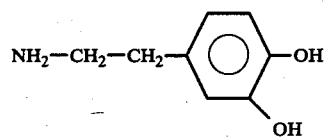

DOPAMINE

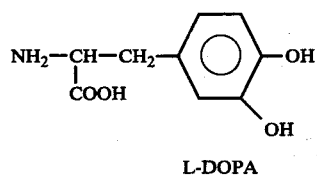

L-DOPA

L-DOPA is a compound that is metabolized in the body of mammals, including man, by aromatic amino acid decarboxylase to dopamine (Christenson et al., Arch. Biochem. Biophys. 141: 356, 1970). Dopamine is a naturally occuring catecholamine considered to be a precursor of norepinephrine. Dopamine plays an important role as a neurotransmitter in the central nervous system and as an inhibitory transmitter in autonomic ganglia. The ability of dopamine to interact with $\alpha$ and $\beta$ receptors in the body often leads to undesirable side effects such as changes in systemic hemodynamics and increases in cardiac output and gangrene. U.S. Pat. No. 3,903,147 and U.S Pat. No. 3,947,590 disclose that this problem is encountered when dopamine is used to increase renal blood flow. U.S. Pat. No. 3,769,424 discloses similar systemic problems when L-DOPA is used as an anti-Parkinson drug to treat disturbances in the brain.

U.S. Pat. No. 3,903,147 and U.S. Pat. No. 3,947,590 disclose the use of a dopamine derivative, γ-glutamyl-dopamine to increase renal blood flow in the kidney without desirable systemic hemodynamic changes. Although these patents disclose the fact that γ-glutamyl-dopamine is a specific renal vasodilator it does not disclose the mechanism by which that effect was achieved.

According to the method of this invention, the γ-glutamyl derivative of DOPA

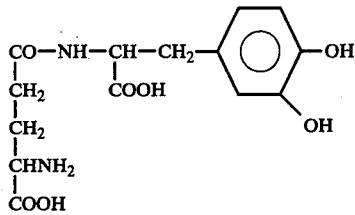

L-γ-glutamyl-L-3,4, dihydroxyphenylalanine
(L-γ-glutamyl-DOPA)

is used as a specific renal vasodilator.

DETAILED DESCRIPTION OF THE INVENTION

Due to the high concentration of the enzyme γ-glutamyl transpeptidase in the kidney, γ-glutamyl-DOPA is kidney specific, and the compound is preferentially concentrated in the kidney by the action of the enzyme. When γ-glutamyl-DOPA is administered to experimental mice, DOPA is released from its glutamyl linkage in the kidney by the action of γ-glutamyl transpeptidase and immediately undergoes enzymatic degradation to dopamine by the action of aromatic amino acid decarboxylase. Since the dopamine is released by enzyme action in the kidney where the pharmacological action is needed, the systemic side effects are minimized.

γ-Glutamyl transpeptidase is an enzyme which is capable of hydrolysing the γ-glutamyl bond of γ-glutamyl peptides as follows:

γ-glutamyl-DOPA + $H_2O$ → glutamate + DOPA

The high concentration of γ-glutamyl transpeptidase in the kidney is shown as follows. If the activity of the enzyme in human kidney is taken as 100, the relative activities in other tissues may be expressed as 8.3 for the pancreas, 3.9 for the liver, 1.5 for the spleen, 0.95 for intestine, 0.5 for the brain, 0.31 for the lung, 0.045 for the heart muscle and 0.067 for skeletal muscle (Orlowski and Szewczuk, Acta Biochem. Polon. 8:189, 1961; Orlowski, Arch. Immun. Therap. Exptl. 11:1, 1963).

Experiments were conducted in which mice were tested to measure the distribution of dopamine in the kidney after administration of γ-glutamyl-DOPA to verify that the L-DOPA that was being released in the kidney was in fact remaining in the kidney and being converted to active dopamine. The following procedure was used to determine the dopamine content of the mouse tissue: Male Swiss-Albino mice weighing 20–25 grams received an intraperitoneal injection of γ-glutamyl-DOPA (0.5 micromole/g) dissolved in 0.15 M NaCl. Twenty minutes after the administration of the drug the animals were decapitated and the kidney, liver, heart, brain, lung, duodenum-pancreas, spleen, and muscle were removed for analysis of dopamine. The tissues were homogenized in five volumes of cold 1 N HCl, cnetrifuged and an aliquot removed and analysed for dopamine by gas chromatography.

It was determined that the dopamine formed from γ-glutamyl-DOPA reached the kidney in approximately the same time as when L-DOPA was administered. A peak level of dopamine was observed 10 minutes after intraperitoneal administration (0.5 μmole/g) of either drug (Table 1).

TABLE 1

| | Dopamine (μg/g) ± Standard Error | |
|---|---|---|
| Time (min) | After γ-glutamyl-DOPA | After L-DOPA |
| 10 | 66.9 ± 14.9 | 23.2 ± 1.9 |
| 20 | 64.5 ± 7.4 | 13.9 ± 1.6 |
| 60 | 9.9 ± 2.3 | 2.6 ± 0.6 |

Tissue levels of dopamine after intraperitoneal administration of γ-glutamyl-DOPA were compared to those found 20 minutes after intraperitoneal administration of 0.5 μmole/g L-DOPA. The data in Table 2 show that the level of dopamine in the kidneys following γ-glutamyl DOPA was considerably higher than when the compound was administered as L-DOPA. In addition, it can be seen, with the exception of the spleen, that when γ-glutamyl DOPA is administered less dopamine is found in organs other than the kidney. This illustrates that the γ-glutamyl-DOPA is being selectively concentrated in the kidney.

TABLE 2

Dopamine distribution in tissues 20 minutes after intraperitoneal administration of γ-glutamyl DOPA or L-DOPA (0.5 μmole/g).

| | Dopamine* (μg/g) ± Standard Error | |
|---|---|---|
| Tissue | After γ-glutamyl-DOPA | After L-DOPA |
| Kidney | 64.5 ± 7.4 | 13.9 ± 1.6 |
| Heart | 2.5 ± 0.5 | 3.2 ± 0.1 |
| Brain | 2.8 ± 0.5 | 2.9 ± 0.3 |
| Liver | 0.6 ± 0.4 | 1.4 ± 0.2 |
| Lung | 0.6 ± 0.2 | 0.9 ± 0.2 |
| Duodenum-Pancreas | 6.1 ± 1.7 | 12.3 ± 2.2 |
| Spleen | 2.3 ± 0.8 | 1.7 ± 0.4 |
| Muscle | 0.2 ± 0.1 | 1.0 ± 0.2 |

*Each value represents the mean ± Standard Error of four determinations.

The ratio of the concentrations of dopamine in the kidney to that of the heart can be used as an index of organ specificity. The higher the ratio, the more kidney specific the compounds. The kidney/heart ratio was 25.8 after administration of γ-glutamyl-DOPA, 4.3 after L-DOPA (Table 1), and 2.5 after dopamine (in the guinea pig, reported by Halushka and Hoffman, J. Pharm. Pharmac. 20:943, 1968). The accumulation of dopamine in the kidney was greater when γ-glutamyl-DOPA was administered. This results in γ-glutamyl-DOPA's being a more efficient and effective form of administering dopamine.

Dopamine is useful as a vasodilator and because of the kidney specificity of γ-glutamyl-DOPA it is useful as a specific renal vasodilator for the treatment of congestive heart failure, shock, hypertension, cirrhosis, acute renal failure, drug intoxication and edema. It has been found that γ-glutamyl-DOPA significantly increases renal blood flow in test rats without the unwanted side effects encountered when DOPA and dopamine are administered in the free form. In experiments, γ-glutamyl-DOPA significantly increased blood flow at doses 40 times lower than the doses of γ-glutamyl-DOPA that were found to cause significant increases in blood pressure.

The tests to measure the increase in renal blood flow after administration of γ-glutamyl-DOPA were carried out in female Sprague-Dawley rats weighing 275-325 grams by determining the clearance of $^{14}$C- p-amino hippurate according to the method of Dick and Davies, J. Clin. Path. 2:67, 1949. Rats were anesthetized with ether and the femoral artery and vein cannulated. The bladder was exposed and catheterized with a #8 polyethylene catheter. The urethra was ligated. An infusing solution of 0.45% saline-p-amino hippurate (PAH) was prepared by diluting normal saline with distilled water and adding 0.025μCi glycyl-1-$^{14}$C-PAH/ml infusing solution (specific activity 43 mCi/mmole). The animals were infused at a rate of 10 ml/hr using a Sage model 355 syringe pump. After a 1 hour equilibration period, urine was collected continuously over 30 minute intervals. Blood was withdrawn from the femoral artery at the midpoint of each 30 minute collection period. A total of 5 collections were made. The effect of γ-glutamyl-DOPA on PAH clearance was studied by adding known concentrations of the drug to the infusing solution.

The mean plasma flow of 2.54 ml/min/100 g was found in control rats. A dose of 5 nmoles/g/30 min γ-glutamyl-DOPA increased the mean plasma flow to 4.8 ml/min/100 g.

In order to determine the side effect, if any, of γ-glutamyl-DOPA on mean arterial blood pressure, animal tests were conducted using 40 times the amount of γ-glutamyl-DOPA that was needed to achieve satisfactory increase in renal blood flow.

Female Sprague-Dawley rats weighing 275-325 g were anesthetized with sodium pentobarbital (50 mg/kg intraperitoneal). The femoral vein and artery were cannulated. The arterial catheter was connected to the blood pressure inducer and blood pressure was recorded with Grass model 7 polygraph. Upon stabilization of arterial blood pressure, the effect of γ-glutamyl-DOPA was evaluated by infusing the drug dissolved in saline into the femoral vein at a constant rate of 10 ml/hr. Increases in systolic pressure of up to 20 mm Hg were observed at a dose of 200 nmole/g/30 min. The blood pressure elevation was gradual. A peak response was obtained 5-17 minutes after initiation of the infusion. These results indicate that the dosage needed to increase renal blood flow (5 nmole/gr 30 min) would not significantly affect arterial blood pressure.

The compound of this invention can be administered as a solution in 0.15 N sodium chloride as an intravenous infusion. The dose can be varied from 5 μmole (1.7 mg) per kg per 30 min up to 150 μmole (52 mg) per kg per 30 min. Sterile aqueous or saline solutions of the compound can be prepared.

The compound of this invention may be prepared by the following methods. The following examples illustrate one novel method of synthesis which is a departure from the general procedure of King & Kidd (J. Chem. Soc. 3315, 1949) and one typical enzymatic synthesis:

EXAMPLE 1

1.97 g of L-DOPA (0.01 mole) was dissolved in 50 ml of 0.5 M $Na_2CO_3$ under nitrogen. The flask was cooled in an ice bath to 0°-5° C. and 5.2 g (0.02 mole) of phthaloyl-L-glutamic anhydride, dissolved in 30 ml of dry dioxane was added dropwise with stirring. The mixture was stirred for an additional 20 minutes and then acidified to approximately pH 1.0 by the addition of 6 M HCl. The mixture was extracted with several portions of ethyl acetate and the pooled extracts were dried with anhydrous, solid sulfate. Ethyl acetate was removed from the extract by flash evaporation and the residue was dissolved in 50 ml methanol. 3 ml of hydrazine hydrate (99%) were added to the methanol solution and the mixture was left for 2 days at 26° C. Methanol was then removed by flash evaporation and the residue was suspended in 50 ml of water. The suspension was acidified to pH 3.0 by the dropwise addition of 1 M HCl. The precipitated white solid (phthaloyl hydrazide) was removed by filtration and the filtrate was adjusted back to pH 5.0. The solution was then applied at 4° C. to the top of a Dowex-1 (acetate) column (2.5 × 45 cm). The column was washed with 100 ml of 0.01 M acetic acid and then eluted with a linear gradient established between 2 liters of 0.01 M acetic acid and 2 liters of 2 M acetic acid. Fractions of approximately 20 ml were collected. The presence in the eluate of ninhydrin-positive material is determined by a spot test on Whatman No. 1 filter paper. The product of the reaction emerged from the column when approximately 2 liters of the eluent passed through the column. The fractions containing γ-glutamyl-DOPA were pooled and acetic acid was completely removed by flash evaporation under reduced pressure at 37° C. An amorphous white solid was obtained. The yield was 1.4 g (43%) L-γ-glutamyl-L-3,4-dihydroxyphenylalanine (γ-glutamyl-DOPA).

| Microanalysis for $C_{14}O_7N_2H_{18} \cdot H_2O$ | |
| --- | --- |
| Calculated % | Found % |
| C 48.84 | 49.39 |
| H 5.85 | 6.02 |
| N 8.14 | 7.42 |

EXAMPLE 2

Enzymatic synthesis of γ-glutamyl-DOPA

Glutathione and L-DOPA were incubated with a partially purified preparation of sheep kidney γ-glutamyl transpeptidase. γ-Glutamyl-DOPA was isolated from the incubation mixture by preparative ion exchange chromatography on a Dowex-1 (acetate) column. 6.14 of glutathione (0.02 mole) and 1.97 g of L-DOPA (0.01 mole) were dissolved in 200 ml of 1 M Tris (base) solution. 2.5 ml of γ-glutamyl transpeptidase solution (100 units/ml) were added and the flask was flushed with nitrogen to protect DOPA from oxidation and the mixture was incubated at 37° for 6 hours. L-γ-glutamyl-L-3,4-dihydroxyphenylalanine (γ-glutamyl-DOPA) was isolated by ion exchange chromatography as in Example 1. It emerges from the column when approximately 2 liters of the eluent passed through the column. Unreacted. glutathione, free glutamate and cysteinylglycine emerge from the column in earlier fractions.

Both the chemically and enzymatically prepared compounds were identical. A singly ninhydrin positive spot with an Rf of 0.32 was obtained on paper chromatography (Whatman No. 1. paper) in a solvent system consisting of 1-butanol-pyridine-water (1:1:1). A single peak was also observed on amino acid analysis using the Technicon TSM amino acid auto-analyzer and a lithium citrate buffer system.

Although the compound has been isolated in the form of the free acid, addition salts with organic bases can be prepared by conventional procedures. For example, an addition salt with the basic amino acid arginine has been prepared by reacting equivalent amounts of γ-glutamyl-DOPA and arginine base in methyl alcohol and isolating the precipitated salt.

We claim:

1. A method for increasing renal blood flow in mammals which comprises administering a dose, effective to increase renal blood flow, of a compound:

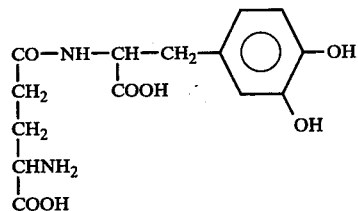

2. A method for increasing renal blood flow in mammals which comprises administering by injection a dose, effective to increase renal blood flow, of a compound:

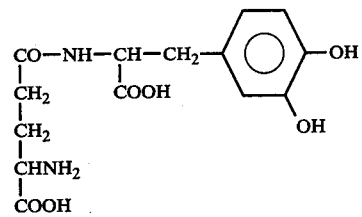

* * * * *

UNITED STATES PATENT OFFICE
CERTIFICATE OF CORRECTION

PATENT NO. : 4,125,626
DATED : November 14, 1978
INVENTOR(S) : Orlowski et al.

It is certified that error appears in the above-identified patent and that said Letters Patent are hereby corrected as shown below:

First page, Item 54, "L-y-Glutamyl-DOPA" should read --L-GAMMA-GLUTAMYL-DOPA--;

Col. 1, line 1, "L-y-GLUTAMYL-DOPA" should read --L-GAMMA-GLUTAMYL-DOPA --;

Col. 1, line 62, "desirable" should read --undesirable--;

Col. 2, line 61, "cnetrifuged" should read --centrifuged--;

Col. 4. line 37, "dosage" should read --dosages--;

Col. 4, lines 59 & 60, "acidfied" should read -- acidified--;

Col. 4, line 63, after "solid" insert --sodium--.

Signed and Sealed this

First Day of May 1979

[SEAL]

Attest:

RUTH C. MASON
Attesting Officer

DONALD W. BANNER
Commissioner of Patents and Trademarks